United States Patent [19]

Avery

[11] Patent Number: 5,393,462
[45] Date of Patent: Feb. 28, 1995

[54] REUSABLE THERMAL PACK AND FLOW RETARDANT GEL FOR USE THEREIN

[75] Inventor: John R. Avery, Athens, Tenn.

[73] Assignee: P.I., Inc., Athens, Tenn.

[21] Appl. No.: 168,916

[22] Filed: Dec. 15, 1993

Related U.S. Application Data

[60] Continuation of Ser. No. 869,541, Apr. 15, 1992, abandoned, which is a division of Ser. No. 794,726, Nov. 15, 1991, abandoned.

[51] Int. Cl.$^6$ ............................ C09K 5/00; B01J 13/00
[52] U.S. Cl. .................................. 252/315.5; 252/71; 604/291; 607/114; 62/530
[58] Field of Search ................ 252/315.5, 71; 514/944; 604/291, 114; 62/4, 530; 128/399, 403; 106/632

[56] References Cited

U.S. PATENT DOCUMENTS

| | | | |
|---|---|---|---|
| 2,710,008 | 6/1955 | Jensen | 128/403 |
| 3,075,529 | 1/1963 | Young, Jr. | 128/403 |
| 3,780,537 | 12/1973 | Spencer | 62/530 |
| 3,871,376 | 3/1975 | Kozak | 128/403 X |
| 4,428,844 | 1/1984 | Wagener | 507/104 |
| 4,439,328 | 3/1984 | Moity | 507/104 X |
| 4,462,224 | 7/1984 | Dunshee et al. | 62/530 |
| 4,568,392 | 2/1986 | Dawson et al. | 507/144 |
| 4,925,603 | 5/1990 | Nambu | 264/28 |
| 5,043,019 | 8/1991 | Chervenak et al. | 106/632 X |

OTHER PUBLICATIONS

Webster's II new Riverside University Dictionary, (The Riverside Publishing Co., Boston, Mass) pp. 474–484.

Gray, George Robert, *Compositions and Properties of Oil Well Drilling Fluids, Fourth Edition*, (Gulf Publishing Company, 1980) pp. 580–583.

*Hawley's Condensed Chemical Dictionary, 11th Edition*, (Van Nostrand Reinhold Co., New York 1989) p. 128.

Primary Examiner—Robert L. Stoll
Assistant Examiner—Daniel S. Metzmaier
Attorney, Agent, or Firm—Lee, Mann, Smith, McWilliams, Sweeney & Ohlson

[57] ABSTRACT

A thermal pack for heating or cooling portions of a body and a flow retardant gel for use therein. The thermal pack includes a gel pad and a pressure chamber. The gel includes a fibrous material disposed therein to essentially prevent flow and increase heat capacity.

9 Claims, 2 Drawing Sheets

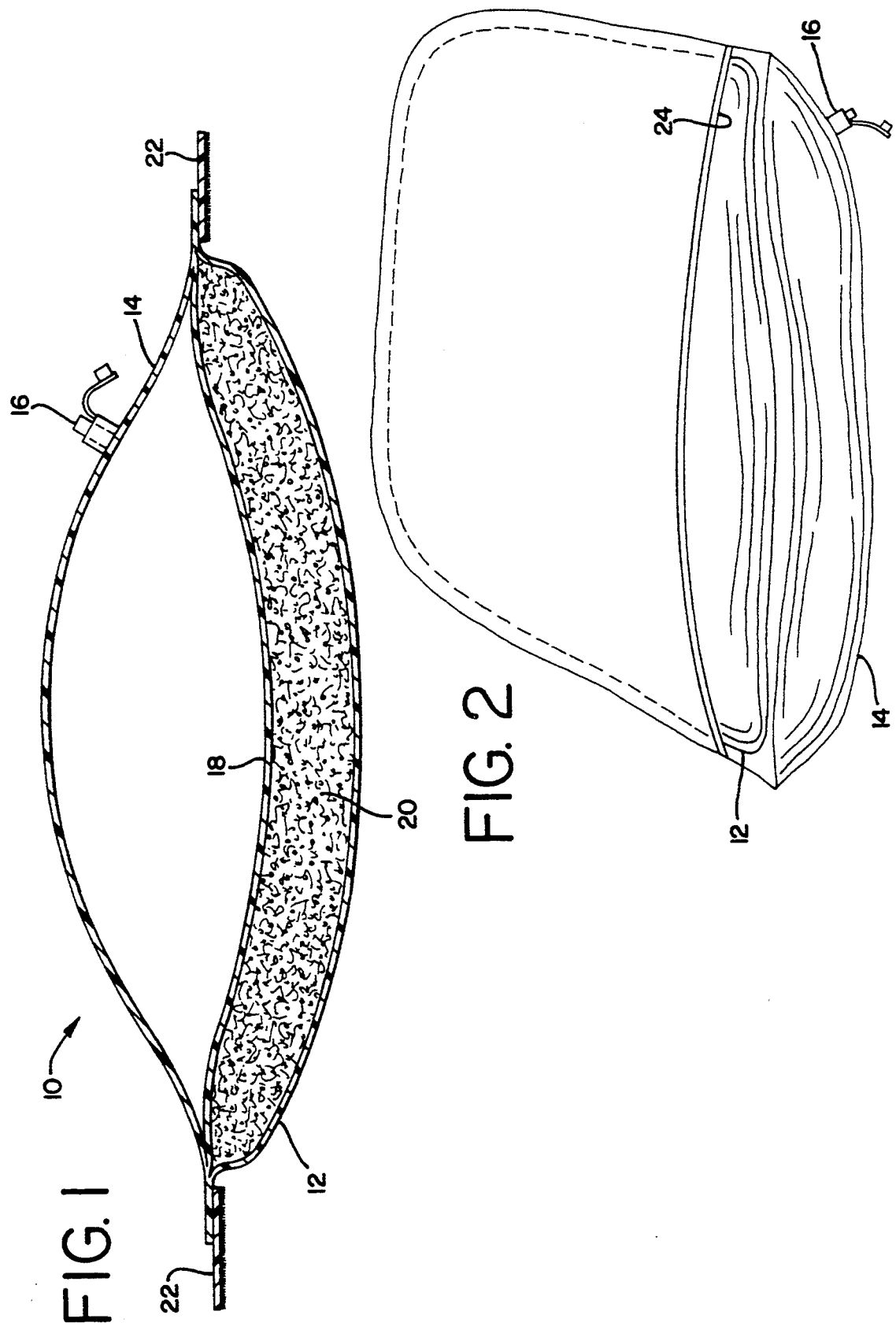

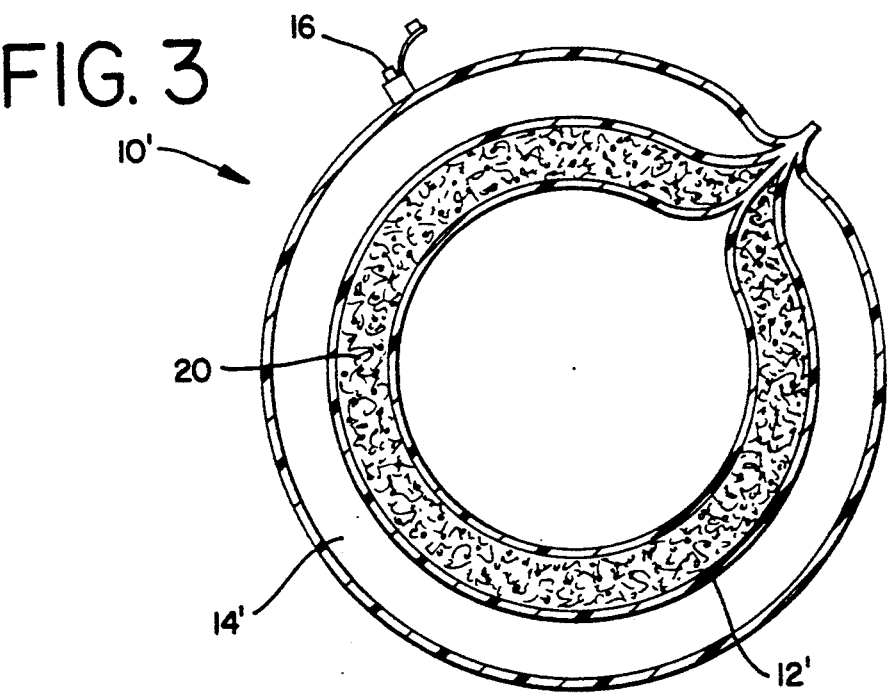
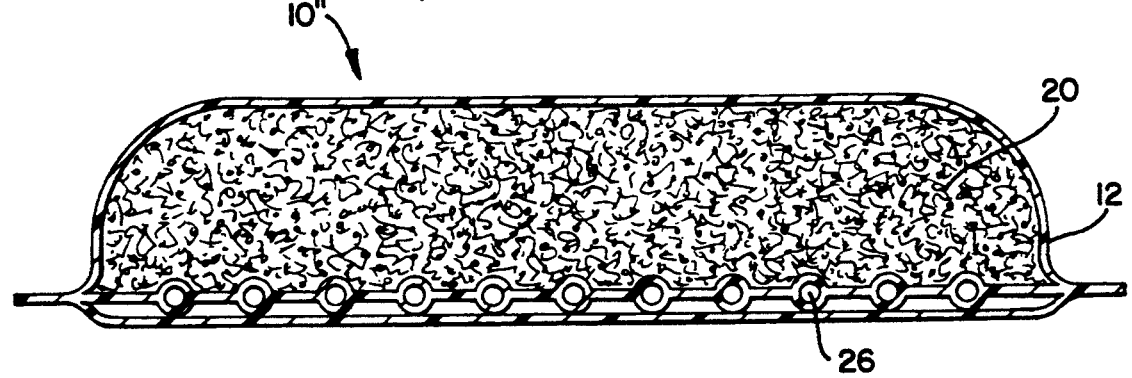
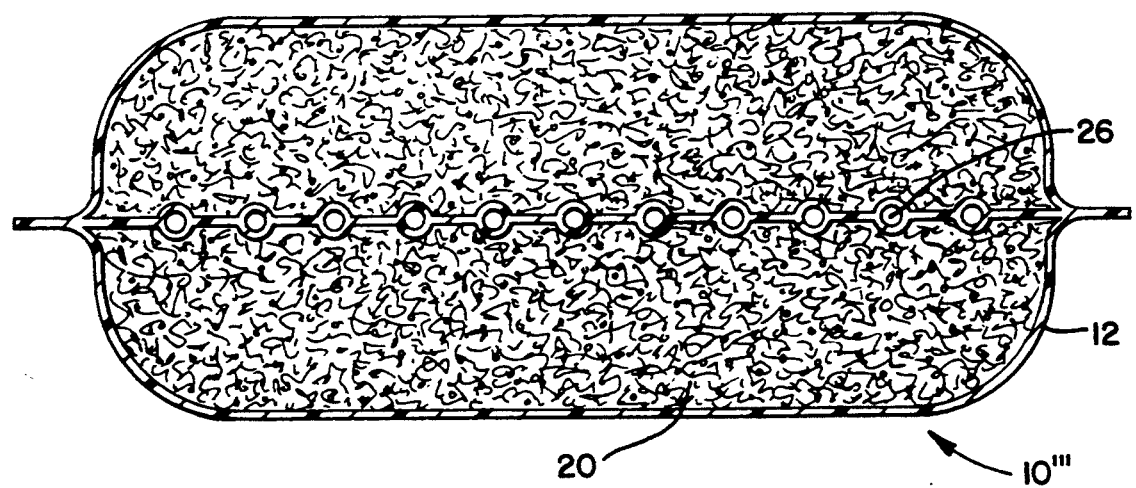

REUSABLE THERMAL PACK AND FLOW RETARDANT GEL FOR USE THEREIN

This application is a continuation of application Ser. No. 07/869,541, filed Apr. 15, 1992, abandoned, which is a division of application Ser. No. 794,726, filed Nov. 15, 1991, abandoned.

BACKGROUND OF THE INVENTION

This invention relates to a thermal pack and gel for use therein, and more particularly to a thermal pack having a gel pack and a separate pressure chamber which can be inflated and deflated and a flow retardant gel for use therein for use on sore or injured body portions.

Ice packs and heat packs have proved their therapeutic usefulness for treatment of aches, pains, sprains and the like and have taken on new significance in the field of medicine, particularly sports related medicine. It has been well recognized that heat, cold and pressure alone or in various combinations may be helpful aids to therapy and first aid. Conventional heat packs or cold packs require the use of straps, tape or wrap to hold them in place, making them difficult and often messy to use. Additionally, it is difficult to surround a limb and to supply uniform contact over the entire area.

Various methods of providing heat and cold to injuries have been used. Most common is the ice pack which uses a conventional polymer bag with crushed ice or ice cubes enclosed therein, or a fluid that is endothermic and which is activated one time by breaking an encapsulated pouch. A more advanced example of an ice pack is a plastic bag or pouch containing an extremely viscous flowable gel material of water, glycol and clay. Common disadvantages of conventional gels are that they include fast flow rates, or high motility, so that when the pack is used the gel will flow or migrate rapidly away from all pressure points, thereby thinning out over the area to which the gel is most needed and thickening at the periphery where it is least useful. Additionally, the gel may migrate rapidly downward in response to gravity from areas of the pad which are in a vertical position. This diminishes the effectiveness of the pad in application of heat or cold.

Previously, the only means of providing a combination of heat and pressure or cold and pressure has been to use the conventional heat or cold packs in conjunction with tape or elastic bandages or other wrapping material. These methods make it extremely difficult to supply even pressure and even heating or cooling of the desired surface.

SUMMARY OF THE INVENTION

The present invention provides a reusable thermal pack which includes an inner pad or pads which encapsulate a gel or other semi-solid medium, and an external inflatable and deflatable pressure chamber, or chambers. Reusable thermal packs of this type can be made to conform to a pillow or pad-like configuration, a tube configuration or any number of various configurations. Additionally, a means for circulating liquid through a chamber or chambers situated adjacent to or embedded within the gel pad or pads can be incorporated to provide for continuous heating or cooling of the gel or semi-solid medium.

Additionally, a flow retardant gel having a slow or negligible flow rate, or low motility rate compared with conventional gels and a higher heat capacity compared with conventional gels is provided. Such a flow retardant gel includes a fibrous, flaked or shredded material included in the gel.

The resultant reusable thermal pack provides a means for applying heat, cold or pressure, or any combination of these therapies in conjunction with one another to a body portion. The pack can be easily designed to conform to body parts without the need for tape, bandages or other wrappings to hold it in place during use. Additionally, the pack assures more uniform contact between the hot or cold pack with the affected area. Also, the flow retardant gel provides for a uniform heating or cooling system which does not flow away from pressure points or flow due to the influence of gravity when in a vertical or elevated position.

BRIEF DESCRIPTION OF THE DRAWINGS

The invention is described in greater detail in the following detailed description of examples embodying the best mode of the invention, taken in conjunction with the drawing figures, in which:

FIG. 1 is a cross-sectional view of one embodiment of the present invention,

FIG. 2 is a perspective view of an embodiment of the present invention incorporating a pocket for the insertion of either the gel pad therein, FIG. 3 is a cross-sectional view of an additional embodiment of the invention in the form of a tube, FIG. 4 is a cross-sectional view of yet another embodiment of the invention incorporating a means on one side for circulating liquid to continuously heat or cool the gel of the present invention, and FIG. 5 is a cross-sectional view of still another embodiment of the invention which includes an internal means for circulating liquid to continuously heat or cool the gel.

DETAILED DESCRIPTION OF THE PREFERRED EMBODIMENTS

A first embodiment of a thermal pack according to the invention is shown generally at 10 in FIG. 1. The thermal pack 10 includes two basic portions, a gel bag or pad 12 and a pressure bag or chamber 14 disposed contiguous to and coextensive with the gel pad 12. A conventional valve 16 is disposed in the pressure chamber 14 for inflation and deflation of the pressure chamber 14. The gel pad 12 has an outer shell made of a flexible membrane material such as polyvinyl chloride or any other suitable material. The pressure chamber 14 has an outer shell made of a similar flexible membrane material. In the form illustrated the gel pad 12 and the pressure chamber 14 share a common wall 18. The gel pad 12 and pressure chamber 14 may be conformed into any shape or size and the gel pad 12 may be similar or dissimilar to the shape of pressure chamber 14. Additionally, the gel pad 12 may include openings and/or void areas or shapes. Both the gel pad 12 and the pressure chamber 14 may be a single or multi-chambered unit.

A gel 20 is disposed within the gel pad 12 and is a semi-rigid colloidal dispersion of a solid with a liquid which retains heat or cold depending on the temperatures to which the pack 10 has been subjected. While suitable flow retardant gel 20 will be discussed herein, the thermal pack 10 is adapted for use with any other suitable gel material.

A fastening means or closure, such as a hook and loop fastener 22, may be included on or in conjunction with the thermal pad to aid in positioning or holding the device in place during use. Such fastening means or closure can include but is not limited to buckles, clasps, clips, snaps, buttons and hook and loop fasteners.

As shown in FIG. 2, the gel pad 12 may be separate from the pressure chamber 14 (rather than sharing a common wall 18 as in FIG. 1), and the thermal pack 10 may include one or more pockets or envelopes 24 into which the gel pad 12 or pressure chamber 14 may be inserted. It is preferred that if a pocket 24 is employed, the pocket 24 be sealed or include means for sealing so that the encapsulated gel pad or pressure chamber does not inadvertently fall out.

In use, the pressure bag chamber 14 is inflated via the valve 16 and remains at a constant internal pressure in use until the pressure is adjusted. If the pressure chamber 14 is a multi-chambered unit, pressure may vary between the individual chambers. Additionally, the pressure chamber 14 provides external insulation for the gel pad 12 thereby allowing the gel pad 12 to retain heat or cold for longer periods of time. This arrangement allows for the uniform cooling or heating of an affected area while applying both pressure and heat or cold therapy. The pack 10 may be of any size and shape such as a pillow, cushion, wedge, collar, mask, bolster, mat, mattress, sling or cradle.

Another embodiment of the invention is shown in FIG. 3. This embodiment illustrates a tubular pack 10' that includes a gel chamber or pad 12' and an external pressure chamber 14'. The external pressure chamber 14' includes a valve 16 to allow for inflation and deflation of the pressure chamber 14'. The pressure chamber 14' is disposed adjacent the gel pad 12' and both are conformed into a tubular shape. This tubular shape allows an affected limb or body part to be inserted therethrough and surrounded for treatment. Alternatively, a non-tubular form which is wrapped around the body part to conform into a generally tubular shape can be used. The non-tubular form can be shaped into a tube and be held in such form with a zipper, hook and loop fastener, snaps or buttons, or simply by friction.

When the external pressure chamber 14' is filled with air via the valve 16, an even amount of pressure is exerted on the inner gel pad 12' and provides for an even cooling or heating therapy and even pressure therapy. The inflated pressure chamber 14' also holds the thermal pack 10' in place on a limb and can allow for more mobility of a patient during treatment. The pressure chamber 14' also provides insulation for the gel pad 12' thereby allowing the gel pad 12' to retain heat or cold for longer periods without reheating or refreezing. The shape of form shown in FIG. 3 is tubular. However, several variations of this tubular shape may be made, such as a cuff, sleeve, cap, boot or vest.

As shown in FIGS. 4 and 5, a fluid heat exchanger 26 can be included in the thermal pack 10" or 10'''. Such a fluid heat exchanger 26 includes liquid tubes in serpentine or maze configurations situated adjacent to or embedded within the gel pad 12 to increase, decrease or vary the temperature of the gel 20 in the gel pad 12. A liquid, not shown, can be circulated through the tubes to provide for temperature variations in the gel 20. Such a pack provides for a more even distribution of temperature because the gel pad 12 can conform to the shape of a body part. The gel pad 12 provides a semi-insulative barrier between the heat exchanger 26 and the body part, and more evenly distributes the heat or cold of the circulated fluid. Thus, the temperature of the circulating fluid can be changed easily and quickly, yet the gel 20 of the gel pad 12 will change gradually. In this manner, the user will be less likely to experience discomfort or injury due to exposure to extreme temperatures.

The flow retardant gel 20 of the present invention will now be discussed. The gel 20 has a slow flow rate, or low motility as compared with conventional gels and a higher heat capacity as compared with conventional gels. Consequently, the gel 20 will not migrate or flow from the pressure points or in response to gravity, thereby retaining more gel 20 over the desired area for a longer period of time than conventional gels. Additionally, because of the increased heat capacity of the gel 20, a thermal pack incorporating such a gel retains its heating and cooling capacity for longer periods of time, thus making such a pad more convenient. The gel 20 of the preferred embodiment includes a mixture of clay, water and fibrous material. Also, for gels used in cold pads a substance to lower the freezing point is necessary. Such a substance can include glycol or sodium. Such a gel should contain, by weight, approximately 15% to 30% clay, 0% to 75% water, 1.0% to 10% fibrous material and 0% to 60% of a substance to lower the freezing point. A mixture of 23.5% clay, 33% glycol, 41% water and 2.5% fibrous material has proven particularly effective. However, various percentages of clay, water, fiber and glycol can be combined to provide satisfactory results so long as the resulting gel has a slow or negligible flow rate.

The preferred clay is Bentonite type clay in fine grain form. However, any suitable clay material can be used. The preferred glycol is propylene glycol. However, any other suitable substance can be used to lower the freezing point, such as introduction of a salt into the water employed. The fibrous material can be in the form of fibers, flakes and shreds of any size. The fibers may be individual fibrils, monofilaments, slivers, ribbons or combined as woven or non-woven or plated or twisted fibers, strands, ribbons or threads. A preferred fibrous material is nylon 66. However, any suitable fibrous material can be used. The preferable length of the fibers of the fibrous material ranges from $\frac{1}{4}$ inch to $\frac{1}{2}$ inch. Individual fibers, flakes or shreds may be freely suspended within the gel or attached to each other, or to a substrate or multiple substrates which may be freely suspended or attached to one or more of the walls of the pad. It is the fibrous material that gives the gel its unique property of extremely low or negligible flow.

ACHIEVEMENTS

Several advantages are realized with the introduction of the fibrous material into the gel. A greater percentage of water and/or glycol can be incorporated into the gel mixture without adversely affecting the flow restrictive properties of the gel. The greater the amount of water or glycol added to the gel, the greater the heat absorption of the gel. Therefore, the use of the fibers also increases the heat capacity of the gel thereby providing a more efficient gel for use in thermal packs. Additionally, the resultant gel has an extremely low or essentially non-existent mobility as compared with conventional gels. Consequently, the gel will not migrate from the pressure points or flow in response to gravity, thereby providing for a far more effective resultant thermal pack.

While the gel 20 is essentially non-flowing, it is flexible in combination with the plastic material forming the gel pad and the pressure chamber. In any form of the invention, the thermal pack conforms readily to the surface of the patient, no matter how irregular that surface may be. Thus, application of heat or cold therapy is applied directly to the area being treated without any substantial insulative air layer or other insulation reducing the efficiency of the thermal pack.

In the tubular form of the invention as shown in FIG. 3, when the thermal pack is applied about a limb being treated and the pressure chamber is inflated, the thermal pack is held snugly in place. No additional fasteners, hooks or other means of holding the thermal pack are necessary in this form of the invention, a substantial improvement over all other prior art devices that use fasteners or straps to hold their devices in place.

In addition to its utility to hold the tubular form of the invention in place, the pressure chamber, when employed, forms an effective insulant between the ambient atmosphere and the gel, so that the therapeutic value of the gel is directed to the patient being treated, and is not lost to the atmosphere. In all other commercial devices, no such insulant is used, and therefore a substantial percentage of the therapeutic value of the devices is lost due to convection and conduction to the surrounding atmosphere or any other object in contact with the device.

Various features of the invention have been shown and described in connection with the illustrated embodiments of the invention. However, it must be understood that these particular arrangements merely illustrate, and that the invention is to be given the fullest interpretation within the terms of the appended claims.

What is claimed is:

1. A non-flowing gel for use in thermal packs for human treatment, said gel comprising a mixture of materials comprising
   clay, a liquid and a fibrous or flake material;
   the clay being a clay substrate in an amount of from about 15% to 30% by weight;
   the liquid including a glycol and water wherein the water is in an amount of from about 0% to 75% by weight; and
   the fibrous or flake material being of sufficient concentration to impart a negligible flow rate in said gel and provide uniform contact between the hot or cold pack with the affected area, wherein said sufficient concentration is from about 1% to 10% by weight;
   the gel being a semi-rigid, non-flowing, extremely viscous mixture comprising a colloidal dispersion of a solid with a liquid.

2. A gel as in claim 1 comprising a salt as an additional component of said gel for lowering the freezing point of said gel.

3. A gel as in claim 1 wherein said glycol is propylene glycol.

4. A gel as in claim 1 wherein said proportion of clay to water to fibrous material to glycol is preferably 23.5/41/2.5/33 by weight.

5. A gel as in claim 1 wherein said clay substrate is bentonite.

6. A gel as in claim 1 wherein said fibrous or flake material is fibers or shreds.

7. A gel as in claim 1 wherein said fibrous or flake material includes fibers of from $\frac{1}{4}$ to $\frac{1}{2}$ inch in length.

8. A gel as in claim 1 wherein said fibrous or flake material is nylon 66.

9. A gel as in claim 1 wherein said liquid further includes up to 60% glycol by weight.

* * * * *